United States Patent
Rach et al.

(10) Patent No.: US 12,213,738 B2
(45) Date of Patent: Feb. 4, 2025

(54) METHOD, APPRATUS AND COMPUTER PROGRAM FOR CREATING MANUFACTURING DATA FOR AN ORTHOPEDIC PRODUCT

(71) Applicant: OTTOBOCK SE & CO. KGAA, Duderstadt (DE)

(72) Inventors: Olaf Rach, Duderstadt (DE); Pierre Chabloz, Saint Georges de Commiers (FR); Uli Maier, Berlin (DE)

(73) Assignee: OTTOBOCK SE & CO. KGAA, Duderstadt (DE)

(*) Notice: Subject to any disclaimer, the term of this patent is extended or adjusted under 35 U.S.C. 154(b) by 424 days.

(21) Appl. No.: 17/838,394

(22) Filed: Jun. 13, 2022

(65) Prior Publication Data

US 2022/0401149 A1 Dec. 22, 2022
US 2023/0132357 A2 Apr. 27, 2023

(30) Foreign Application Priority Data

Jun. 15, 2021 (DE) .................... 10 2021 115 467.7

(51) Int. Cl.
*A61B 34/10* (2016.01)
*A61F 2/50* (2006.01)
*G06T 7/11* (2017.01)

(52) U.S. Cl.
CPC ............ *A61B 34/10* (2016.02); *A61F 2/5046* (2013.01); *G06T 7/11* (2017.01); *A61B 2034/102* (2016.02);
(Continued)

(58) Field of Classification Search
CPC ............... F23G 7/061; F23G 2207/101; F23G 2207/20; F23G 2207/30; F23G 2207/112;
(Continued)

(56) References Cited

U.S. PATENT DOCUMENTS

2019/0019347 A1* 1/2019 Auvray ................ G06T 7/0012
2019/0152138 A1* 5/2019 Zhao ...................... B29C 64/35

FOREIGN PATENT DOCUMENTS

DE 10 2008 032 992 A1 1/2010
DE 102018124516 A1 * 4/2020
(Continued)

*Primary Examiner* — Kidest Bahta
(74) *Attorney, Agent, or Firm* — WC&F IP (57) ABSTRACT

The invention relates to a method for creating manufacturing data for manufacturing an orthopedic product for a body part of a patient, the method comprising the following steps:
providing a digital three-dimensional body part model of the relevant body part for which the orthopedic product is destined to an electronic data processing apparatus, the three-dimensional body part model being based on external body part data acquired from the body part of the patient;
identifying at least one rigid body part region in the provided body part model by means of the electronic data processing apparatus, with the remaining region situated outside of the rigid body part region being identified as a yielding body part region on the basis of the identified rigid body part region;
creating a reduced three-dimensional body part model by means of the electronic data processing apparatus on the basis of the provided three-dimensional body part model, the identified rigid body part regions and a reduction metric applied in the region of the yielding body part region; and
producing manufacturing data for the orthopedic product on the basis of the reduced three-dimensional body part model by means of the electronic data processing apparatus.

17 Claims, 6 Drawing Sheets (52) U.S. Cl.
CPC ... *A61B 2034/105* (2016.02); *A61B 2034/108* (2016.02)

(58) Field of Classification Search
CPC .......... F23G 2207/113; F23G 2207/40; F23G 5/165; F23G 2204/103; F23G 2204/20; F23G 7/063; F23G 7/065; B01D 53/44; B01D 2258/02; B01D 2257/708; B01D 53/72; F23J 15/04; F23J 2900/15061; F23J 15/06; F23N 1/022; F23N 5/102; F23N 2227/02
See application file for complete search history.

(56) References Cited

FOREIGN PATENT DOCUMENTS

| | | |
|---|---|---|
| DE | 10 2019 109 781 A1 | 10/2020 |
| DE | 2019 122 374 A1 | 2/2021 |
| EP | 1 843 291 A1 | 10/2007 |

\* cited by examiner

METHOD, APPRATUS AND COMPUTER PROGRAM FOR CREATING MANUFACTURING DATA FOR AN ORTHOPEDIC PRODUCT

The invention relates to a method for creating manufacturing data for manufacturing an orthopedic product for a body part of a patient. The invention likewise relates to an apparatus and a computer program in this respect.

Orthopedic products within the meaning of the present invention are orthoses and prostheses in particular. Orthoses are products that support, assist, protect or restrict the freedom of movement of a body part of the patient, for example a joint, in order to avoid overuse. By contrast, prostheses replace lost or missing body parts of the patient.

Below, a patient is understood to mean any user of the orthopedic product. Consequently, this is the wearer of the product to be produced.

Every orthopedic product is arranged on a body part of the patient. In this case, there need not necessarily be contact with the skin of the patient. By way of example, orthoses are frequently worn over clothing such that the latter, for example a pair of trousers, is situated between the orthopedic product and the skin of the patient. Nevertheless, a knee orthosis, for example, is fastened to the knee or the leg of the patient. A prosthesis always comprises an interface element which is connected to an amputation stump or any other body part and which is fastened to the respective body part. By way of example, a prosthesis socket that represents the interface between the prosthesis and the amputation stump is used in the case of a leg prosthesis. In this case, the amputation stump would be the body part of the patient. As a rule, a liner is used between the skin surface of the amputation stump of the patient and the prosthesis socket in order to reduce shearing forces that act on the skin.

As a rule, a prosthesis socket for an amputation stump is manufactured from a stiff (hardly deformable) material, for example a fiber-reinforced plastic, and forms an important part of the interface between the amputation stump and the prosthesis, which is arranged on the prosthesis socket. Corresponding prosthesis sockets have been used for a long time, especially for leg prostheses which are intended to be arranged on an amputation stump, for example a thigh stump. However, the invention is not restricted to this type of prosthesis sockets. Prosthesis sockets of the type described here can also be used for arm prostheses or below-knee prostheses.

Prosthesis sockets for leg amputees, in particular, are exposed to particular loads during daily use. When walking, the entire weight of the patient rests on the prosthesis socket and hence, in particular, on the amputation stump arranged in the prosthesis socket. It is therefore of the utmost importance to adapt the prosthesis socket as optimally as possible to the individual conditions and needs of the patient, in particular to the shape and geometry of the relevant body part.

Therefore, the prior art has disclosed a number of different methods with which the shape and embodiment of the prosthesis socket should be adapted to the amputation stump under load. As a rule, a mold of the amputation stump is made to this end in order to obtain a blank and a base body, on which the prosthesis socket is constructed. Making a mold of the stump by means of plaster for the purposes of creating a negative form of the stump still is dominant today. In addition to the low costs, this method is advantageous in that skilled orthopedic technicians can already influence the shape of the subsequent prosthesis socket by way of targeted shaping of the amputation stump when applying the plaster. This is particularly advantageous if the subsequent socket should have specific load-bearing zones.

To be able to apply a load on the amputation stump that is as uniform as possible, there has been an increased development of methods in which a uniform pressure is exerted on the amputation stump while the shape of the amputation stump is recorded. In the process, the stump is arranged in a water-filled volume, for example, such that the water can exert a uniform pressure. A sand-filled volume can also be used as an alternative to a water bath. However, it is disadvantageous that such methods are not very transportable for constructional reasons and consequently find little application in daily clinical use.

Optical scanning methods, in which the amputation stump is gauged by optical camera devices, are known from the prior art. However, even if such a method is usable, the amputation stump is only gauged statically. As a rule, it is not possible to acquire data while the amputation stump is moving. Moreover, it is generally not possible to deform the amputation stump by virtue of building up pressure, for example by using hands, and to capture the amputation stump deformed in this way.

All the aforementioned methods known from the prior art have the disadvantage that the mold of the relevant body part, in particular an amputation stump, ignores the loads on the relevant body part that occur during intended use. The models arising accordingly only offer an insufficient description of reality. Accordingly, it is necessary to resort to the experience of an orthopedic technician when producing an orthopedic product. Hence, a test socket is often produced first, which is tested on the patient and has to be worn by the latter. In this way, a check is carried out as to whether the socket meets the requirements or whether changes are necessary. Optionally, the shape of the test socket must be adapted to a dynamic situation if the test socket discloses problems and sub-optimal shaping. This is time consuming and costly.

DE 10 2019 122 374 A1 has disclosed a method for producing an orthopedic product for a body part of a patient, in which body part data are depicted from a current viewing direction by means of a display device such that the user sees the body part and the body part data in overlaid fashion. Then, production data are generated on the basis of the depicted data and a corresponding orthopedic product is produced.

DE 10 2019 109 781 A1 has disclosed a method for creating manufacturing data for manufacturing an orthopedic device, the latter being producible within the scope of an automated manufacturing method using the created manufacturing data. In this case, a digital volume model of the orthopedic device to be manufactured is created on the basis of a digital functional form, which contains a 3-D body part model of a body part, and the digital manufacturing data are generated from the digital volume model.

The invention is therefore based on the object of proposing a method for producing an orthopedic product for a body part of a patient, which overcomes or least reduces the disadvantages.

According to the invention, the object is achieved using the method according to claim 1. Advantageous embodiments of the invention can be found in the corresponding dependent claims.

According to claim 1, a method is proposed for creating manufacturing data for manufacturing an orthopedic product for a body part of a patient, in which a digital three-dimensional body part model of the relevant body part for which the orthopedic product is destined is initially provided to an electronic data processing apparatus. In this case, the digital three-dimensional body part model contains the external shape and geometry of the relevant body part of the patient in particular, and consequently represents a digital impression of the relevant body part. In particular, such a digital impression was acquired in such a way here that it was created without additional load on the relevant body part. Rather, this is a model of the body part in the unburdened state. In this case, the three-dimensional body part model is based on external body part data acquired from the body part of the patient, these external body part data being able to be acquired by means of a digital scan, for example. Other imaging methods or molding mechanisms are also conceivable here.

A liner may have also initially been pulled over the body part; it also has a certain influence on the shape of the body part as a result of its elastic embodiment. Since the liner is frequently also worn under the subsequent orthopedic product (which is also referred to as an orthopedic device), it is advantageous to include this in the impression (e.g., scan). Advantageously, use is always made of the same liner, which is subsequently also worn under the orthopedic product.

Subsequently, one or more rigid body part regions are detected in the body part model, said body part regions not yielding, or only yielding insubstantially, in the case of a pressure load on account of their anatomical nature of the body part. In contrast to muscle tissue, connective tissue, soft tissue and the like (yielding body part regions), such rigid body part regions do not experience compression when the orthopedic product is used and consequently only have restricted suitability for receiving loads. As a rule, such rigid body part regions are formed by rigid body structures situated directly below the skin or very close under the skin, for example by scarring or bones. On the basis of the identified rigid body part regions, the remaining regions situated away from the rigid body part regions are identified as yielding body part regions. The yielding body part regions are those regions of the body part that yield under a load or stress and can be compressed. Such yielding body part regions are characterized by muscle tissue, connective tissue and other soft tissue in particular.

Finally, a reduced three-dimensional body part model is created; it is intended, in terms of the shape and geometry, to digitally reproduce the body part under load or stress. The reduction ensures that the orthopedic product will subsequently be seated securely and with good fit on the body part and will be able to absorb loads. The loads arising during use in the case of a prosthesis, in particular, must be reliably transferred to the body part. In this case, this reduced three-dimensional body part model is created on the basis of the provided 3-dimensional body part data, the identified rigid body part regions and a reduction metric. In this case, the reduction metric is applied in a region of the yielding body part regions in order to take account of the yield of these yielding body part regions as a result of the orthopedic product itself during the subsequent use of the orthopedic product to be produced as these regions have the best suitability for absorbing loads. This may comprise the entire yielding body part region or else only a portion thereof.

Then, the manufacturing data for the industrial manufacture of the orthopedic product are produced on the basis of the reduced three-dimensional body part model that has been created.

With the aid of the present invention it becomes possible to create manufacturing data for an orthopedic product which is adapted individually to a body part of a very specific patient and, in the process, circumvent the disadvantages from the prior art in relation to making a mold of the body part in the unloaded state. With the aid of the reduction metric, it is possible in this case to, in a targeted manner, compensate the yield of the soft body part regions and ignore the rigid body part regions in this reduction such that a particularly good comfort of wear can be obtained. In this case, the method according to the invention is particularly suited to the automated production of such orthopedic products, without test products having to be created to this end. Complicated manual post-processing is dispensed with.

Consequently, a user (for example, an orthopedic technician) of the method can create an orthopedic product which takes account of compressions and deformations occurring when the body part is under load and accordingly compensates these for a good and secure comfort of wear, without the user of the method needing to develop a prototype of the orthopedic product for the patient.

The body part can be an arm, for example an upper arm or a forearm, a leg, for example a thigh or a lower leg, or a joint, for example a hip joint, a knee, an ankle or an elbow. For prostheses and prosthesis sockets in particular, the body part can also be an amputation stump, for example a thigh stump, a below-knee stump, or an arm stump.

The identification of the rigid body part regions and, conversely, also the yielding body part regions is implemented in automated fashion here by means of the electronic data processing apparatus, such that a fully automated process for producing an orthopedic product arises. It is possible in the process for markings to have been applied to the body part, said markings making it easier for the electronic data processing apparatus to identify the position of the anatomical regions, especially the rigid body part regions, in automated fashion. In this case, the orientation and/or the extent of the rigid body part regions in particular are automatically determined by the electronic data processing apparatus and assigned to the respective positions.

In this case, the three-dimensional body part model is reduced in selected regions of the yielding body part regions in accordance with the reduction metric such that this yields a reduced extent and/or a reduced volume of the three-dimensional body part model. Reducing the volume of the three-dimensional body part model in the yielding body part regions ensures a secure seat of the product on the body part, and a stress under load when using the orthopedic product is modeled and then is input in the orthopedic product to be produced. In this case, the result is the reduced three-dimensional body part model.

According to an embodiment, provision is made for the provision of an orthopedic product produced on the basis of the manufacturing data. In this case, the creation of the orthopedic product on the basis of the manufacturing data produced according to the invention can in particular be implemented in an automated manufacturing method, within the scope of which the orthopedic product is produced substantially without human intervention. Such an orthopedic product can also be a shape model which represents a copy of the body part and which is used to produce a prosthesis or orthosis.

An automated manufacturing method using an automated production line is understood to mean, in particular, a method in which the orthopedic device produces the orthopedic device without interposition of human intellectual activity and without manual intervention. By way of example, such an automated manufacturing method can be an additive or generative manufacturing method, for example a 3-D printing method. However, subtractive methods such as CNC milling, for instance, are also conceivable. In this case, such automated manufacturing methods can also be subsumed by the term "rapid manufacturing process".

In this case, it is possible either for the orthopedic product itself to be produced or for a shape model of the body part to be produced initially from the manufacturing data as an intermediate step, the orthopedic product then being produced on the basis thereof (for example by deep-drawing). Manufacturing data are understood within the scope of the present invention to mean not only the data that serve directly to manufacture the orthopedic product but also those manufacturing data that can be used to produce intermediate products, for example a shape model of the body part, with the actual orthopedic product then being produced on the basis of these intermediate products.

In addition thereto, it is for example also possible to produce splint systems, joints, braces or other components of an orthosis, which take account of the individual nature of the patient, for example sizes and lengths of certain body parts such as, e.g., arms and legs, position and orientation of different body parts in relation to one another and movement options and movement restrictions, for example of joints. This is particularly advantageous in the case of braces that are ordered directly for and adapted to a body part of the patient, and that come into direct contact with this body part during the subsequent use of the orthopedic product.

Provision is made according to an embodiment for the provision of the body part model to comprise the acquisition of body part data on the basis of a digital scan of the relevant body part of the patient by means of a scanning apparatus and the creation of the three-dimensional body part model on the basis of the acquired body part data by means of the electronic data processing apparatus. The body part and the liner, which is applied over the body part to the skin of the patient, are generally scanned in this case.

By way of example, the body part data can be acquired by means of a scanning apparatus. By way of example, the latter can be a scanning liner or a scanning glove. By way of example, if the body part is an amputation stump, use can be made of a scanning liner, which is pulled over the amputation stump and which is able to detect its own geometric shape. By way of example, this can be implemented by way of strain gauges within the liner, which determine the distance between precisely defined points of the liner. If this is implemented over a sufficiently large portion of the liner, preferably over the entire liner, it is possible to determine the contour and geometric shape of the liner, and hence also the geometric shape and contour of the amputation stump contained within the liner.

As an alternative or in addition thereto, scanning gloves can be used even where body parts, for example arms, legs, feet or joints, are present. These comprise sensors which for example can measure and determine absolute positions so that the geometric shape and the external contour of the body part can be detected and gauged, for example by virtue of the user of the method sweeping over the skin of the body part while wearing a scanning glove.

By way of example, fiber Bragg sensors, ultrasonic sensors or magnetic sensors, which render the external shape of the body part detectable, are appropriate sensors used in the scanning glove or in the scanning liner.

The body part data preferably are 3-dimensional body part data.

According to an embodiment, provision is made for electronic data processing apparatus to be used to simulate at least one joint axis of a joint of the body part in the digital three-dimensional body part model so that the digital three-dimensional body part model can be moved about the at least one joint axis into an initial position. In this case, the movement of the body part model by way of a rotation about the joint axis can in particular be implemented in automated fashion by the electronic data processing apparatus.

In this case, the joint axes are preferably recognized automatically by the electronic data processing apparatus. By way of example, this can be implemented by way of an augmented body part model. In this case, a generic anatomical model which may also comprise further information such as the relative position of bones and soft tissue in addition to information about the joint axes is modified and individualized by means of the scan data. As a result, the external contour then corresponds to the scan data while use can be made of the further information in the augmented body part model. In this case, the digital body part model can be rotated and brought into an advantageous initial position so that an optimal production of the manufacturing data can be ensured. This is because the position of the patient during scanning is frequently not sufficiently controllable and in disadvantageous/extreme flexion positions, as a result of which the body part changes in a manner that is undesirable for the production. By way of example, an initial position with the flexion position between 10° and 15° is provided for a knee joint.

According to an embodiment, provision is made for the three-dimensional body part model to be displayed in overlaid fashion with the at least one identified rigid body part region on a display that is connected to the electronic data processing apparatus.

The regions that are rigid body part regions and not affected by the reduction metric and the regions identified as yielding regions that are subject to a reduction on the basis of the reduction metric are indicated to the user of the method in this way. Consequently, the result of the reduction can also be presented to the user of the method, for example by virtue of the original, unchanged body part model being presented overlaid on the body part model that has been reduced on the basis of the reduction metric. Optionally, the user of the method can intervene manually and further reduce or attenuate certain regions which, in their experience and with comprehensive knowledge of the patient, are subject to greater compression.

Consequently, the user of the method, for example an orthopedic technician, still can implement manual changes to the data in order thus, for example, to take account of certain properties of the body part. By way of example, the user is able to attach markings to the body part model, which are subsequently taken into account when producing the reduced three-dimensional body part model. By way of example, it thus is possible to mark regions in which padding should subsequently be arranged.

Different materials that should be used in the product to be produced can also be assigned to different regions in this way.

Furthermore, it may be advantageous in the method to implement further changes in the digital body part model. Thus, it may be advantageous to change the length of the body part in order thus to be responsive to different compression properties of different liners or else take account of expected changes of the soft-tissue distribution in the body part. In the case of such changes, it is once again advantageous to exclude the rigid body part regions since there cannot be any changes in length there. A volume redistribution of the soft tissue can be achieved by the change in length. It may also be advantageous to increase the body part regions identified as rigid (for example, design the socket to be wider such that no/less pressure is exerted on these regions) and thus provide for an additional unburdening of these sensitive regions.

In the case of a below-leg socket, three rigid regions, in particular, are of particular importance and are identified accordingly by the method: head of fibula, tibia and patella. In the case of a forearm, these are the epicondyles of the humerus and the olecranon.

According to an embodiment, provision is made for the orientation and/or extent of the at least one rigid body part region in relation to the body part model to be determined automatically using the electronic data processing apparatus. To this end, appropriate markings may be provided for on the digital three-dimensional body part model O, which markings are used in particular for the automated identification of the position of the rigid body part regions.

According to an embodiment, provision is made for anatomical body part data of the body part of the patient to be provided to the electronic data processing apparatus, with the rigid body part regions on the provided body part model being identified automatically by means of the electronic data processing apparatus on the basis of the provided anatomical body part data.

By way of example, the provision of the anatomical body part data may be based on an imaging medical method and said anatomical body part data are stored, for example, in an electronic data memory to which the electronic data processing apparatus has access. By way of example, the medical method can be a CT (computed tomography) method, an MRI (magnetic resonance imaging) method or any other imaging method. These data are often present in any case, as they were recorded and acquired following the operation. Alternatively or in addition thereto, corresponding body part data may be recorded within the scope of the method described here and may be subsequently provided.

However, alternatively or in addition, it is also conceivable for the three-dimensional body part model of the patient, the known orientation of the body part model and basic anatomical knowledge about the body part represented by the three-dimensional body part model to be used as a basis for automatic determination of the rigid structures, for example the bone structures, contained therein and for these rigid structures to serve as a basis for determining the rigid body part regions. Although this does not use the exact data of the patient, this is sufficient in most cases for a close enough approximation for determining the rigid body part regions.

According to an embodiment, provision is made for the three-dimensional body part model to be reduced in at least a part of the yielding body part region before the creation of the reduced three-dimensional body part model on the basis of the reduction metric. In this case, provision can be made for the three-dimensional body part model to be copied, with a corresponding reduction only being implemented in the copy. In this case, the copy can be augmented with further properties, for example joint axes in order to thus be able to move the body part model in the style of the body part to be modeled. This also allows recognition and identification of regions which require particular attentiveness on account of a movement about the joint axis. This allows identification, in particular also automated identification, of cutout regions for facilitating sufficient movement about the joint axis.

According to an embodiment, provision is made for less than 10%, preferably less than 8% to be reduced on the basis of the reduction metric. In this case, the percentage specification can be related to the extent at the corresponding position that should be reduced, or orient itself globally in respect of the entire volume of the body part model.

According to an embodiment, provision is made for the degree of reduction to vary from proximal to distal over the body part length on the basis of the reduction metric. Accordingly, the reduction metric is designed such that, proceeding from a position on the body part model, the reduction changes over the length of the body part from proximal to distal.

According to an embodiment, provision is made for the measure of reduction to be defined on the basis of the reduction metric, depending on a reduction position at which a reduction should be carried out. Hence, the degree of reduction can change depending on the position on the body part model.

The measure of reduction, for example the percent of the extent or the volume that should be removed at the respective position, in this case varies within the yielding body part regions and depends on the position within the body part model.

According to an embodiment, provision is made for one reduction metric from a multiplicity of reduction metrics to be selected on the basis of a liner material. In this case, different reduction metrics can be created for different materials of the liners, with the appropriate reduction metric then being chosen depending on the employed material.

Hence, the selection of the reduction metric depends on the liner material, in particular on its flowability, in particular in the case of flowing liner materials such as polymers, polyurethanes and copolymers, with a smaller reduction being provided for proximally than distally, in particular increasing over the course from proximal to distal. The liner material is flowable and should flow away distally upwardly as a result of the greater reduction.

According to an embodiment, provision is made for one reduction metric from a multiplicity of reduction metrics to be selected on the basis of a property of the body part. By way of example, such a property can be the shape of the body part, so that conical shapes are for example reduced more significantly than cylindrical ones. Thus, properties such as, e.g., the body part geometry and the soft-tissue state, can be used as a basis for the selection of an appropriate reduction metric. Thus, the selection of the reduction metric may also depend on a soft tissue status or soft-tissue state, with for example atrophied and normal body parts being reduced more significantly than body parts with a high soft-tissue component.

For the purposes of creating the reduced three-dimensional body model by means of the electronic data processing apparatus, provision is made according to an embodiment for the reduction metric to be applied in the region of the yielding body part region in a first step and for at least one rigid body part region to be increased in a second step.

According to an embodiment, provision is made for the length of the body part model to be adapted in a further step and, in the process, for the body part regions identified as rigid to remain unchanged.

According to an embodiment, provision is made for the body part to be an amputation stump and for the orthopedic product to be a socket, preferably for the lower extremities.

According to an embodiment, provision is made for more than one, preferably 2, particularly preferably 3 rigid regions to be identified.

Furthermore, the object is also achieved by the apparatus according to claim 16 for carrying out the above-described method, with the apparatus having at least one electronic data processing apparatus for carrying out the method. In this case, the electronic data processing apparatus can be connected to a scanning apparatus for acquiring external body part data and optionally be connected to a production line in order to produce the orthopedic product in automated fashion on the basis of the created manufacturing data.

Furthermore, the object is also achieved by the computer program according to claim 17, with the computer program having program code means which are configured to carry out the above-described method when the computer program is executed on a data processing apparatus.

The present invention is now described in more detail in exemplary fashion with the aid of the attached drawings, in which.

Figure 1:
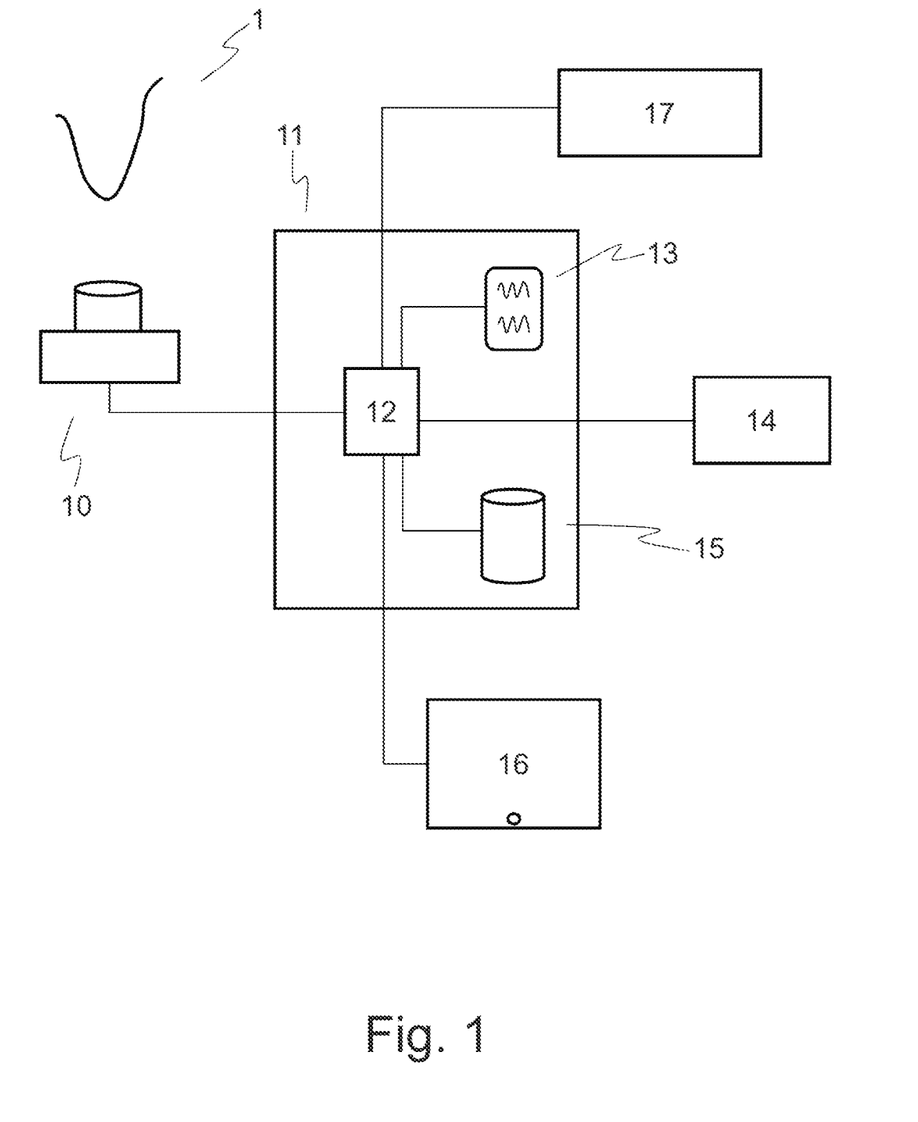
FIG. 1 shows a schematic representation of method flows.

FIG. 1 schematically shows a structure and method flow of the present invention. A body part 1 of the patient (not depicted here) is digitally scanned with the aid of a scanning apparatus 10. The resultant scan data are transmitted to an electronic data processing unit 11, which can carry out the present method by way of its electronic computing unit 12. In the exemplary embodiment of FIG. 1, the body part 1 relates to an amputation stump of a leg.

To carry out the present method, the electronic computing unit 12 of the electronic data processing apparatus 11 is provided with a reduction metric 13 in order to be able to carry out the reduction of the body part model in accordance with said reduction metric 13. In this case, the provision of a plurality of reduction metrics is conceivable, with different reduction metrics being selected depending on the property of the relevant body part, for example geometry, soft-tissue state and/or liner material.

Moreover, appropriate anatomical body part data may be provided to the electronic data processing apparatus 10 from a medical method 14 so that the rigid body part regions can be identified accordingly. However, it is also conceivable for data corresponding to the body part 1 to be provided to the electronic computing unit 12 with the aid of a database 15, said data facilitating an automated determination of rigid body part regions.

With the aid of a display 16 it is possible to display the respective method steps to a user of the present method, who is thus given the option to intervene in the production of the model and the data.

Once the appropriate manufacturing data were created with the aid of the electronic computing unit 12 of the electronic data processing apparatus 11, these can be transmitted to an automated production line 17 such that a corresponding orthopedic product can be produced on the basis of the manufacturing data. In this case, the step of the automated production line 17 may contain a mold of the body part 1 being created on the basis of the reduced 3-dimensional body part model in an automated manufacturing method, as may also be produced when making a mold of the body part 1 using plaster. Then, the relevant orthopedic product can be created on the basis of a body part mold produced thus. The body part mold produced, which was created on the basis of the reduced three-dimensional body part model, in this case contains the deformation of the body part 1 under load and thus explicitly adapts to the needs of the patient.

FIGS. 2 to 6 will now explain, in exemplary fashion, the procedure up to the production of the reduced 3-dimensional product model.

Figure 2:
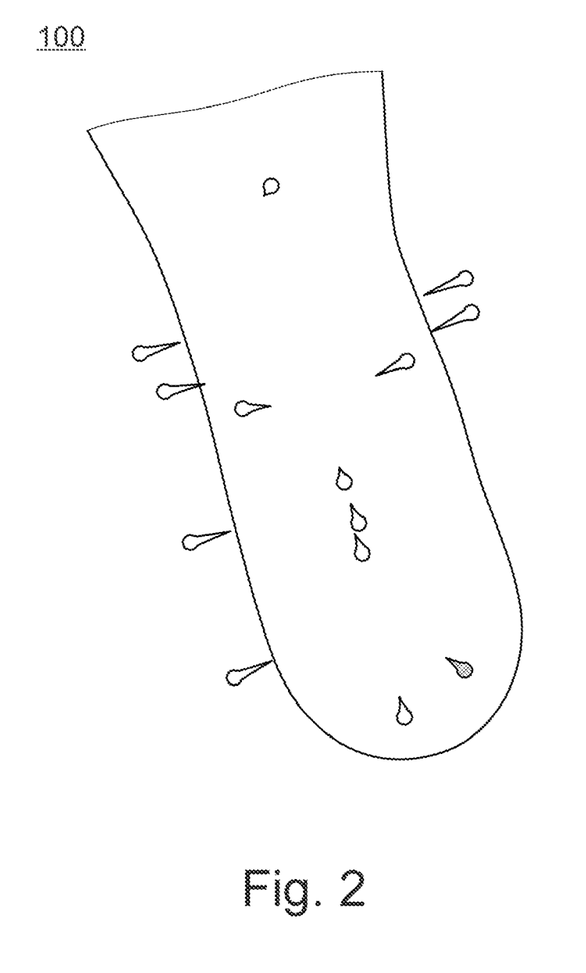
FIG. 2 shows a representation of scan data of a scan.

FIG. 2 shows a digital scan 100 of the body part 1, for which an orthopedic product should be produced. The body part which was digitally acquired for the production of the digital scan 100 is an amputation stump of a leg, with the amputation being implemented below the knee.

The markings shown in FIG. 2 may in this case have been applied by a user of the method, for example an orthopedic technician, and may represent boundary conditions or optionally also rigid body part regions.

Figure 3:
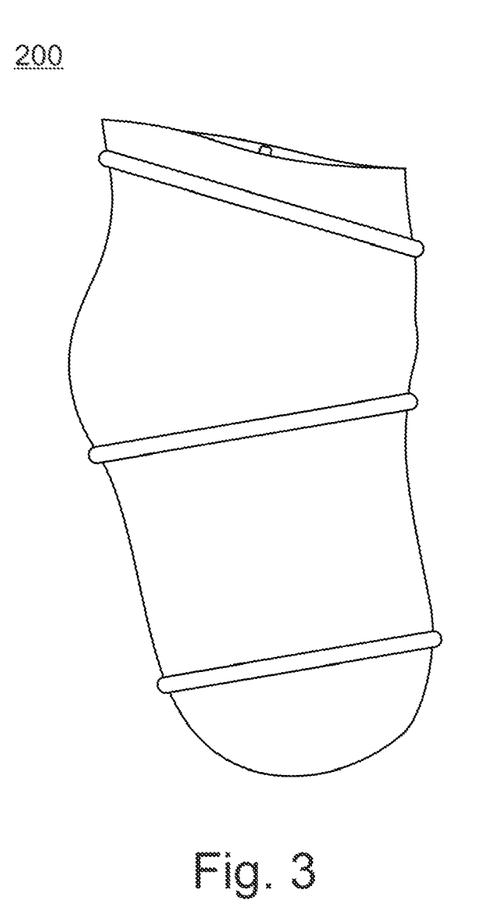
FIG. 3 shows a representation of an avatar.

Subsequently, what is known as an avatar 200, which is represented in FIG. 3 and which in contrast to the scanning model implements movement properties, is created on the basis of these scan data, which are also referred to as external body part data. Thus, for example, the avatar can be rotated and movements can be carried out in the actual model itself. By way of example, a joint axis can be inserted into the avatar in order thus to be able to digitally map movements of the body part with the aid of the still present joint. In this way, the scan can be recorded in the simplest position but the avatar can subsequently nevertheless be brought into the position required for the socket construction.

In this case, rigid structures, for example bones or scarring, and yielding body part regions, for example muscles, connective tissue and soft tissue, can be represented in overlaid fashion in the avatar.

Figure 4:
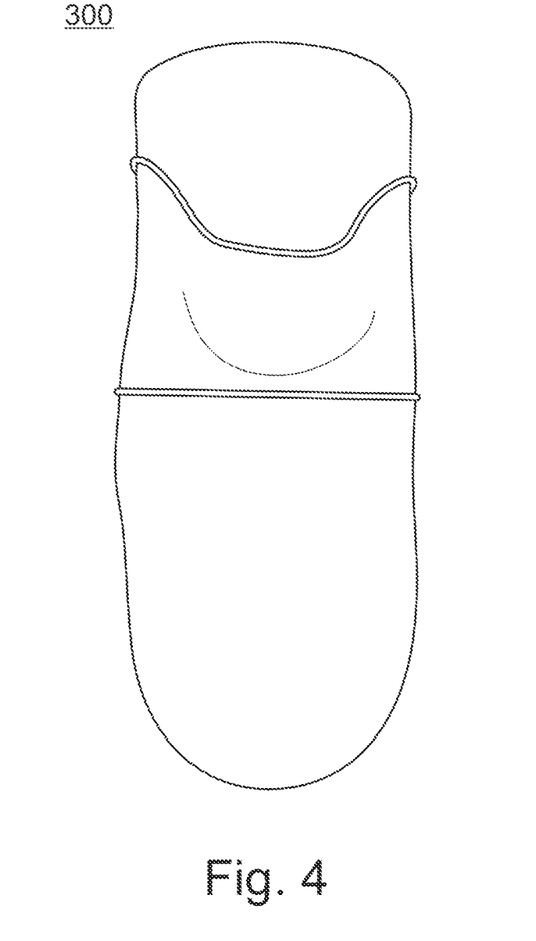
FIG. 4 shows a representation of a body part model.

Once the avatar 200 has been aligned appropriately, a digital three-dimensional body part model 300 is created on the basis thereof. This is depicted in FIG. 4. Scan data 100 and avatar 200 remain unchanged in this case. This is depicted in FIG. 4.

Figure 5:
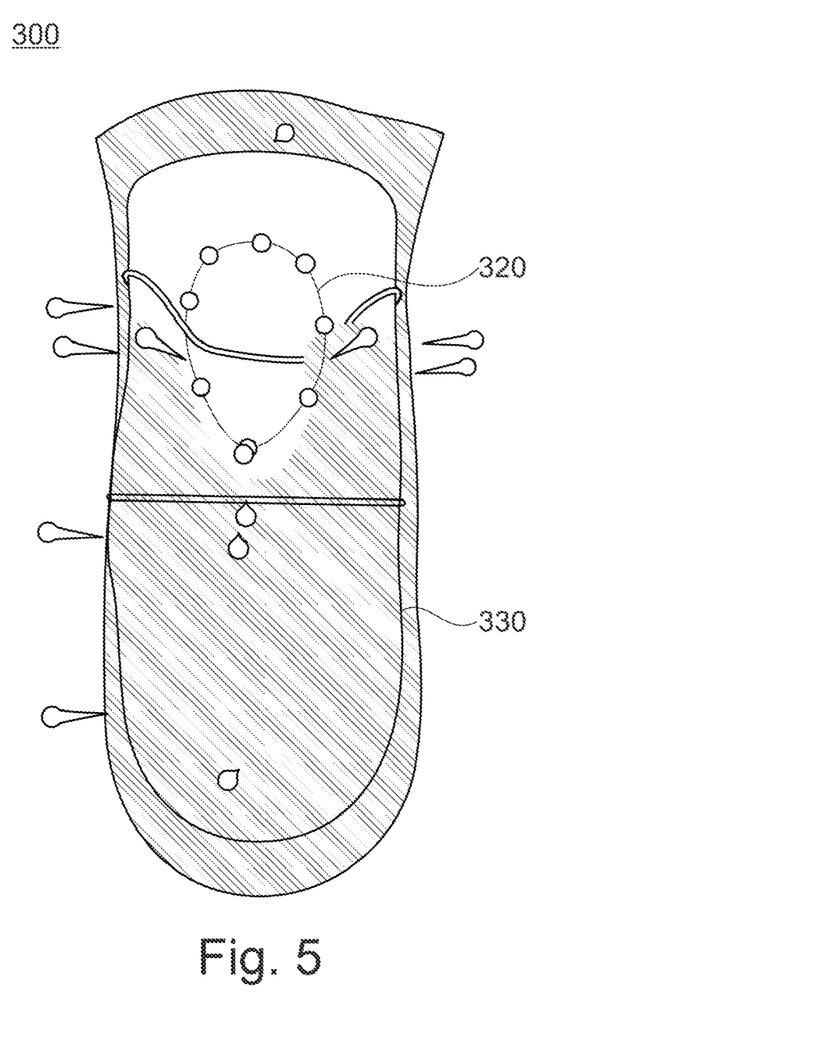
FIG. 5 shows a representation of a body part model with rigid body part regions.

Now, the rigid body part regions 320 are subsequently identified, as depicted in FIG. 5. In the present exemplary embodiment, the rigid body part region is the kneecap (patella) which was identified on the basis of anatomical body part data of the patient or in general terms. In this case, the markings created by the orthopedic technician may also serve as indications. In this case, the remaining regions are identified as yielding body part regions 330.

In this case, the user of the method can manually improve the dimensions of the rigid body part regions 320 should the automated recognition not have been satisfactory for the user. Subsequently, the further rigid body part regions of tibia and head of fibula can be identified for the present exemplary embodiment and can be manually adapted where necessary (not depicted here). Hence, a total of 3 rigid body part regions are identified in the present exemplary embodiment.

Figure 6:
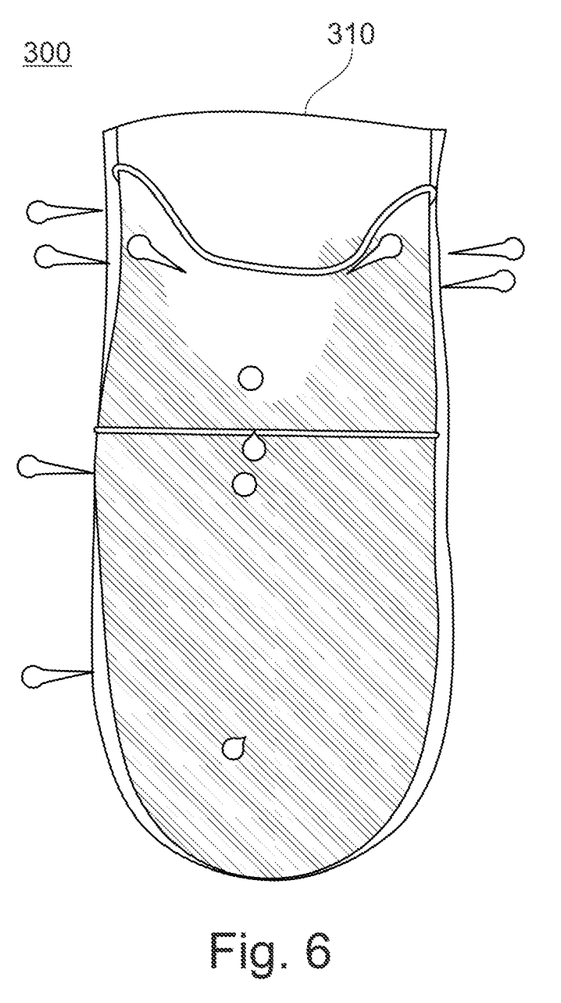
FIG. 6 shows a representation of the reduction in a comparison.

Now, the body part model is reduced in accordance with the reduction metric in order to produce a reduced body part model 310, as is depicted in FIG. 6. The difference between the reduced body part model 310 and the original body part model 300 can be recognized in FIG. 6, there having been no reduction in the region of the rigid body part regions.

According to the reduction metric, the reduction depends on the location or position within the body part model. In this case, provision can be made for the reduction to reduce from distal to proximal. By way of example, provision can be made, starting at the proximal end, for there to be a maximum reduction of 5%, with the reduction being able to increase to up to 10% at the most distal point, with the rigid body part regions not being reduced.

Now, the rigid body part regions can also be adapted to the effect of bringing about an enlargement here. This tends to correspond to the conventional process, in which everything is initially reduced and then reapplied in a few regions. This is an optional step here. However, what is prevented in any case is that there is a reduction at the rigid body part regions. Moreover, it is ensured that the desired overall reduction is achieved.

LIST OF REFERENCE SIGNS

1 Body part
10 Scanning apparatus
11 Electronic data processing apparatus
12 Electronic computing unit
13 Reduction metric
14 Medical method
15 Database
16 Display
17 Anatomical manufacturing data
100 Digital scan
200 Avatar
300 Digital body part model
310 Reduced digital body part model
320 Rigid body part regions
330 Yielding body part regions

The invention claimed is:

1. A method for creating manufacturing data for manufacturing an orthopedic product for a body part of a patient, comprising:
   providing to an electronic data processing apparatus a digital three-dimensional body part model of the body part for which the orthopedic product is to be used, wherein the digital three-dimensional body part model is based on external body part data acquired from the body part of the patient;
   identifying at least one rigid body part region in the provided digital three-dimensional body part model using the electronic data processing apparatus wherein a remaining region is situated outside of the at least one rigid body part region and is identified as a yielding body part region;
   creating a reduced three-dimensional body part model using the electronic data processing apparatus on the basis of the provided digital three-dimensional body part model, the at least one identified rigid body part region, and a reduction metric applied in the yielding body part region; and
   producing manufacturing data for the orthopedic product on the basis of the reduced three-dimensional body part model by the electronic data processing apparatus.

2. A method for producing an orthopedic product, comprising producing the orthopedic product on the basis of manufacturing data created according to claim 1.

3. The method according to claim 1, wherein the step of providing the digital three-dimensional body part model comprises acquisition of body part data based on a digital scan of the body part of the patient by a scanning apparatus and creation of the digital three-dimensional body part model based on acquired body part data by the electronic data processing apparatus.

4. The method according to claim 1, wherein the electronic data processing apparatus is used to simulate at least one joint axis of a joint of the body part in the digital three-dimensional body part model so that the digital three-dimensional body part model is moveable about the at least one joint axis into an initial position.

5. The method according to claim 1, wherein the digital three-dimensional body part model is displayed in overlaid fashion with the at least one identified rigid body part region on a display that is connected to the electronic data processing apparatus.

6. The method according to claim 1, wherein an orientation and/or extent of the at least one rigid body part region in relation to the digital three-dimensional body part model is determined automatically using the electronic data processing apparatus.

7. The method according to claim 1, wherein anatomical body part data of the body part of the patient are provided to the electronic data processing apparatus with the at least one rigid body part region on the body part model being identified automatically by the electronic data processing apparatus based on anatomical body part data.

8. The method according to claim 7, wherein the anatomical body part data is obtained by an imaging medical method.

9. The method according to claim 1, wherein the digital three-dimensional body part model is reduced in at least a part of the yielding body part region for creating the reduced three-dimensional body part model based on the reduction metric.

10. The method according to claim 1, wherein less than 10% of the digital three-dimensional body party model is reduced based on the reduction metric.

11. The method according to claim 1, wherein a degree of reduction varies from proximal to distal over a length of the body part based on the reduction metric.

12. The method according to claim 1, wherein a degree of reduction is defined based on the reduction metric depending on a reduction position at which creating the reduced three-dimensional body part model is to be carried out.

13. The method of claim 1, further comprising selecting the reduction metric from a multiplicity of reduction metrics based a liner material.

14. The method of claim 1, further comprising selecting the reduction metric from a multiplicity of reduction metrics based on a property of the body part.

15. The method of claim 1, wherein the step of creating a reduced three-dimensional body part model comprises applying the reduction metric in the region of the yielding body part region in a first step, and increasing the at least one rigid body part region in a second step.

16. An apparatus for carrying out the method according to claim 1.

17. A non-transient media encoded with a computer program encoded with instructions to carry out the method according to claim 1 when the computer program is executed on a data processing apparatus.

* * * * *